United States Patent [19]

Braga

[11] Patent Number: 5,422,357
[45] Date of Patent: Jun. 6, 1995

[54] METHOD OF USING OXATOMIDE AS ANTITUSSIVE AGENT

[75] Inventor: Piercarlo Braga, Milan, Italy

[73] Assignee: FARKEMO s.r.l., Milan, Italy

[21] Appl. No.: 97,676

[22] Filed: Jul. 27, 1993

[30] Foreign Application Priority Data

Jul. 30, 1992 [IT] Italy .................. MI92A1866

[51] Int. Cl.6 ........................... A61K 31/445
[52] U.S. Cl. ........................ 514/318; 514/850
[58] Field of Search ............ 514/318, 321, 322, 394, 514/395, 850

[56] References Cited

U.S. PATENT DOCUMENTS 4,200,641  4/1980  Vandenberk et al. ............ 514/318

OTHER PUBLICATIONS

Trimarco et al. "Oxatomide: A new drug for the treatment of respiratory allergies" G. Ital Mal Torace 44(4), 1990.

Primary Examiner—Marriane M. Cintins
Assistant Examiner—K. Weddington
Attorney, Agent, or Firm—Bucknam and Archer

[57] ABSTRACT

Oxatomide reduces the number of cough attacks and also prolongs the time between each attack. The effect is dose-related.

2 Claims, No Drawings

METHOD OF USING OXATOMIDE AS ANTITUSSIVE AGENT

The present invention relates to the use of oxatomide as antitussive agent.

Coughing is a useful physiological mechanism which enables the airways to be cleared in a very short time of foreign materials and excess secretions, therefore it should not be suppressed indiscriminately.

Nevertheless, there are situations in which coughing exerts no useful functions, on the contrary it can be disturbing or it can prevent rest and sleep; under these circumstances, the physician can adopt a therapeutical approach to diminish or suppress coughing.

Coughing is a complex reflex involving central Nervous System as well as the smooth muscle or the bronchial tract.

Literature on antitussive drugs has been exhaustively reported by Eddy et al. (Eddy N. B., Friebel H., Hohn K. and Halbach H.: "Codeine and its alternates for pain and cough relief" Bull. WHO, 1969, 40, 639–719) and by Salem and Aviado (Salem H. and Aviado D. M. (eds): "Antitussive Agents, Vols. 1, 2 e 3. International Encyclopedia of Pharmacology and Therapeutics, Sect. 27. Pergamon Press, Ltd., Oxford, 1970).

At present coughing is treated with antitussive drugs classified according to the type of action: direct central action (opioids and nonopioids) or peripheral action (direct and indirect agents).

When chosing a particular drug having central action for a specific patient, the main factors which should be considered are the antitussive effectiveness against pathological coughing and the incidence and nature of the foreseeable side effects.

Now it has surprisingly been found that oxatomide has antitussive activity.

Oxatomide, i.e. 1-[3-[4-(diphenylmethyl)-1-piperazinyl]propyl]-1,3-dihydro-2H-benzimidazol-2-one, is an antiallergic drug useful in asthma in preventing allergic attacks. Such an activity is due to antihistamin, antiserotonin and mastocyte-stabilizing characteristics.

The tests carried out on oxatomide evidenced that this drug can not only decrease the number of coughs, but also increase the time intervals between them. Such an effect is dose-related.

The following example further illustrates the invention.

EXAMPLE

Unanesthetized unrestrained guinea pigs (350–400 g) were placed individually in a transparent plexiglass chamber (10×10×21 cm) and exposed to a nebulized solution of 12% W/V citric acid in saline. The aerosol was produced by an ultrasonic nebulizer (GB-Elbisonic, Italy) and had an aerodynamic mass median diameter of 0.9 μm. Animals were exposed for 3 minutes and 0.5 ml solution was exposed per min. No estimation was made of the citric acid concentration in the box, but all animals were subjected to the same conditions. The guinea pigs were treated with logarithmically increasing doses of oxatomide (0.5, 1, 2 mg/kg) (suspended in 0.5 ml of polyethylene glycol 200+0.5 ml of saline administered intraperitoneally (1 ml) 45 minutes before the challenge. The vehicle (1 ml) without drug was also injected intraperitoneally and tested.

A total of 36 animals were used. The different doses of oxatomide and the vehicle were repeated according a random table and one day of interval was put between the treatments to avoid residual drug effect, so that at the end 36 measures for each dose and vehicle were performed. Each animal was challenged only one time a day and at the end of the study all the animals were tested again with citric acid to control that the reactivity was the same as the first challenge. Dose-response relationships were determined. During the exposure, the animals were watched continuously by a trained observer and the time to the onset of the first cough, the number of coughs during the 3 minutes of challenge and the number of coughs during the 5 minutes immediately after the challenge were recorded. A blind protocol was not required for these measurements, because in this study the control was the vehicle (polyethylene glycol + saline) and there was no comparison with other antitussive drugs.

Animals were selected for the study by the number of outbursts of coughing observed during an aerosol exposure 24 h before the test, animals with more than 18 or less than 6 outbursts were not used for the studies. The differences in the onset of the first cough, in the number of coughs during the 3 minutes of challenge and in the number of coughs during the 5 minutes after the challenge between the different treatments and the controls were tested for significance by analysis of variance among treatments followed, when statistically significant, by multiple pair comparisons according to Dunnet test. These differences were considered statistically significant when the test yielded a value of $p \leq 0.05$.

Exposure to a nebulized solution of 12% citric acid aerosol caused coughing of the selected animals within 62.7±4.0 seconds, while oxatomide at increasing doses produced a significant progressive increase in the latency of the first cough, as shown in Table 1.

TABLE 1

Effects of OXATOMIDE i.p. on coughing induced in guinea pigs by citric acid aerosol

| Parameters (n = 36) | Vehicle | After treatment with Oxatomide (mg/kg i.p.) (mean ± d.s.) | | | Statistical analysis | |
|---|---|---|---|---|---|---|
| | | 0.5 | 1 | 2 | ANOVA | HSD p tSD |
| Time to onset of the 1st cough | 62.7 ±4.0 | 80.4 ±5.4 | 103.9 ±5.4 | 116.0 ±4.9 | $F_{3,105} = 39.7^*$ (**) | 10.65 |
| Number of coughs during the 3 minutes of challenge | 9.4 ±0.5 | 6.8 ±0.4 | 3.7 ±0.2 | 2.4 ±0.2 | $F_{3,105} = 107.4^*$ (**) | 0.86 |
| Number of coughs during the 5 minutes | 10.9 ±0.8 | 6.6 ±0.6 | 3.7 ±0.4 | 2.1 ±0.3 | $F_{3,105} = 113.8^*$ (**) | 1.03 |

TABLE 1-continued

Effects of OXATOMIDE i.p. on coughing induced in guinea pigs by citric acid aerosol

| Parameters (n = 36) | After treatment with Vehicle Oxatomide (mg/kg i.p.) (mean ± d.s.) | | | Statistical analysis | |
| --- | --- | --- | --- | --- | --- |
| | 0.5 | 1 | 2 | ANOVA | HSD p tSD |
| immediately after the challenge | | | | | |

*p < 0.05 Dunnet test
**p < 0.1 ANOVA between treatments

The mean number of coughs during the three minutes in response to the challenge with citric acid was 9.4±0.5. Oxatomide reduced this parameter significantly by 27.9%; 60.6% and 74.7% for the three doses tested. Vehicle, under the same conditions, induced an increase of 4%, which was not significant.

After the time of exposure to chemical stimuli, there is a period of hyperresponsivity and the animals tend to cough spontaneously, without the presence of the citric acid.

Oxatomide can also reduce significantly the number of coughs in the 5 minutes immediately following the challenge.

From the industrial point of view, oxatomide can conveniently be formulated in pharmaceutical compositions according to conventional techniques, for example as described in "Remington's Pharmaceutical Sciences Handbook" Mack Pub., New York, U.S.A. Example of pharmaceutical compositions are injectable solutions or suspensions, suppositories, tablets, capsules, syrups, drops, drinkable solutions, granulates, aerosols.

The dosage will be selected by the physician, depending on the severity of the disorder to treat as well as the age and weight of the patient.

I claim:

1. The method of decreasing cough caused by pathological conditions manifested solely by coughing due to a complex reflex involving the central nervous system, smooth muscle or the bronchial tract and increasing the time interval between one cough and the subsequent cough in a living subject in need of treatment which consists of administering to said living subject a composition containing oxatomide as the active ingredient.

2. The method according to claim 1 wherein said composition is in the form of a solution, a suspension, a suppository, a tablet, a capsule, a syrup, drops, a granulate or an aerosol.

* * * * *